US006627757B2

(12) United States Patent
Fu et al.

(10) Patent No.: US 6,627,757 B2
(45) Date of Patent: Sep. 30, 2003

(54) ENANTIOSELECTIVE SYNTHESIS OF AZETIDINONE INTERMEDIATE COMPOUNDS

(75) Inventors: Xiaoyong Fu, Edison, NJ (US); Timothy L. McAllister, Westfield, NJ (US); T. K. Thiruvengadam, Kendall Park, NJ (US); Chou-Hong Tann, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/105,710

(22) Filed: Mar. 25, 2002

(65) Prior Publication Data

US 2002/0193607 A1 Dec. 19, 2002

Related U.S. Application Data

(60) Provisional application No. 60/279,288, filed on Mar. 28, 2001.

(51) Int. Cl.[7] ............................................. C07D 263/06
(52) U.S. Cl. ................................................... 546/272.4
(58) Field of Search ........................................ 548/230

(56) References Cited

U.S. PATENT DOCUMENTS

| 4,876,365 | A | 10/1989 | Kirkup et al. |
| 5,306,817 | A | 4/1994 | Thiruvengadam et al. |
| 5,561,227 | A | 10/1996 | Thiruvengadam et al. |
| 5,618,707 | A | 4/1997 | Homann et al. |
| 5,624,920 | A | 4/1997 | McKittrick et al. |
| 5,627,176 | A | 5/1997 | Kirkup et al. |
| 5,631,365 | A | 5/1997 | Rosenblum et al. |
| 5,633,246 | A | 5/1997 | McKittrick et al. |
| 5,656,624 | A | 8/1997 | Vaccaro et al. |
| 5,661,145 | A | 8/1997 | Davis |
| 5,688,785 | A | 11/1997 | Vaccaro |
| 5,688,787 | A | 11/1997 | Burnett et al. |
| 5,688,990 | A | 11/1997 | Shankar |
| 5,698,548 | A | 12/1997 | Dugar et al. |
| 5,728,827 | A | 3/1998 | Thiruvengadam et al. |
| 5,739,321 | A | 4/1998 | Wu et al. |
| 5,744,467 | A | 4/1998 | McKittrick et al. |
| 5,756,470 | A | 5/1998 | Yumibe et al. |
| 5,767,115 | A | 6/1998 | Rosenblum et al. |
| 5,846,966 | A | 12/1998 | Rosenblum et al. |
| 5,856,473 | A | 1/1999 | Shankar |
| 5,886,171 | A | 3/1999 | Wu et al. |
| 5,919,672 | A | 7/1999 | Homann et al. |
| 6,093,812 | A | 7/2000 | Thiruvengadam et al. |
| 6,096,883 | A | 8/2000 | Wu et al. |
| 6,133,001 | A | 10/2000 | Homann et al. |
| 6,207,822 | B1 | 3/2001 | Thiruvengadam et al. |
| RE37,721 | E | 5/2002 | Rosenblum et al. |
| 2002/0137689 | A1 | 9/2002 | Glombik et al. |

FOREIGN PATENT DOCUMENTS

| DE | 2046823 A | 3/1972 |
| EP | 0199630 B1 | 10/1986 |
| EP | 0199630 A1 | 10/1986 |
| EP | 0264231 A1 | 4/1988 |
| EP | 0266896 B1 | 5/1988 |
| EP | 0333268 A1 | 9/1989 |
| EP | 0337549 B1 | 10/1989 |
| EP | 0337549 A1 | 10/1989 |
| EP | 0365364 A2 | 4/1990 |
| EP | 0375527 A1 | 6/1990 |
| EP | 0415487 A2 | 3/1991 |
| EP | 0462667 A2 | 12/1991 |
| EP | 0481671 A1 | 4/1992 |
| EP | 0524595 A1 | 1/1993 |
| EP | 0720599 B1 | 7/1996 |
| JP | 136485 | 5/1981 |
| JP | 028057 | 10/1981 |
| JP | 180212 | 3/1986 |
| JP | 121479 | 12/1986 |
| JP | 219681 | 4/1987 |
| JP | 4356195 A | 9/1992 |
| WO | WO 93/02048 | 2/1993 |
| WO | WO 94/14433 | 7/1994 |
| WO | WO 94/17038 | 8/1994 |
| WO | WO 95/08532 | 3/1995 |
| WO | WO 95/26334 | 10/1995 |
| WO | WO 96/16037 | 5/1996 |
| WO | WO 97/16455 | 5/1997 |
| WO | WO 97/21676 | 6/1997 |
| WO | WO 97/41098 | 11/1997 |
| WO | WO 97/46238 | 12/1997 |
| WO | WO 98/01100 | 1/1998 |
| WO | WO 98/05331 | 2/1998 |

(List continued on next page.)

OTHER PUBLICATIONS

Vaccaro et al., "Carboxy–substituted 2–azetidinones as cholesterol absorption inhibitors" *Bioorganic & Medicinal Chemistry Letters* 8:319–322 (1998).

(List continued on next page.)

*Primary Examiner*—Patricia L. Morris
(74) *Attorney, Agent, or Firm*—William Y. Lee

(57) ABSTRACT

The application relates to a process for preparing a compound of Formula I

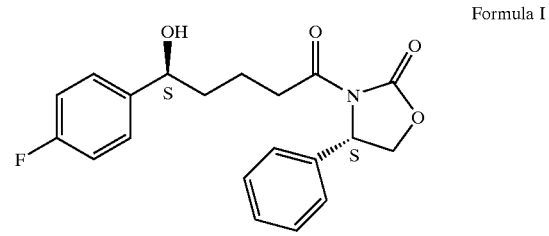

Formula I

This compound is an intermediate used to produce compounds that are useful as hypocholesterolemic agents in the treatment and prevention of atherosclerosis.

20 Claims, No Drawings

FOREIGN PATENT DOCUMENTS

| WO | WO 98/14179 | 4/1998 |
|---|---|---|
| WO | WO 98/31360 | 7/1998 |
| WO | WO 99/18072 | 4/1999 |
| WO | WO 00/20623 | 4/2000 |
| WO | WO 00/34240 | 6/2000 |
| WO | WO 00/60107 | 10/2000 |
| WO | WO 00/63703 | 10/2000 |
| WO | WO 02/50090 A1 | 6/2002 |
| WO | WO 02/066464 A1 | 8/2002 |

OTHER PUBLICATIONS

Vaccaro et al., "Sugar–substituted 2–azetidinone cholesterol absorption inhibitors: enhanced potency by modification of the sugar" *Bioorganic & Medicinal Chemistry Letters* 8:314–317 (1998).

Otto et al., Synthesis and stereochemistry of 3–(α–hydroxy=benzyl)–1,4–diphenyl–2–azetidinones, *Chemical Abstracts* 99(1) (Nov. 7, 1983).

Oguni et al., "Stereoselective syntheses of β–lactam derivatives by ultrasound promoted Reformatskii reaction" *Chemical Abstracts* 106(17) (Apr. 27, 1987).

Hoekman et al., "Synthesis of homologues of . . . Lactones" *J. Agric. Food Chem.* 30:920–924 (1982).

Otto et al., "Darstellung und stereochemie von–3–(α–hydroxybenzyl)–1,4–diphenyl–2–azetidinonen" *Liebigs Ann. Chem.* 1152–1161 (1983).

Georg et al., "3–(1'–hydroxyethyl)–2–azetidinones from 3–hydroxybutyrates and N–arylaldimines" *Tetrahedron Letters* 26(33):3903–3906 (1985).

Hart et al., "An enantioselective approach to carbapenem antibiotics: formal synthesis of (+)–thienamycin" *Tetrahedron Letters* 26(45):5493–5496(1985).

Panfil et al., "Synthesis of β–lactams from α,β–unsaturated sugar δ–lactones" *Heterocycles*, 24(6):1609–1617 (1986).

Ram et al., "Potential hypolipidemic agents . . . phenoxyalkanoates" *Indian Journal of Chemistry* 29B:1134–1137 (Dec. 1990).

Oppolzer et al., "Asymmetric diels–alder . . . Acrylates" *Tetrahedron Letters* 25(51):5885–5888 (1984).

"Ezetimibe: Hypolipidemic cholesterol absorption inhibitor" *Drugs of the Future* 25(7):679–685 (2000).

Rosenblum et al., "Discovery of 1–(4–Fluorophenyl) . . . Absorption" *J. Med. Chem.* 41:973–980 (1998).

Schnitzer–Polokoff et al., "Effects of ACYL–CoA . . . Hamsters" *Comp. Biochem. Physiol.* 99A(4):665–670 (1991).

Horie et al., "Hypolipidemic effects of NB–598 in dogs" *Atherosclerosis* 88:183–192 (1991).

Harwood et al., "Pharmacologic consequences of cholesterol absorption inhibition: alteration in cholesterol metabolism and reduction in plasma cholesterol concentration induced by the synthetic saponin β–tigogenin cellobioside (CP–88818; tiqueside)" *Journal of Lipid Research* 34:377–395 (1993).

Salisbury et al., "Hypocholesterolemic activity of a novel inhibitor of cholesterol absorption, SCH 48461" *Atherosclerosis* 115:45–63 (1995).

Clader et al., "Substituted (1,2–diarylethyl)amide . . . Activity" *J. Med. Chem.* 38:1600–1607 (1995).

Vaccaro et al., "2–Azetidinone Cholesterol Absorption . . . Ring" *Bioorganic & Medicinal Chemistry* 6:1429–1437 (1998).

Sybertz et al. "SCH 48461, a novel inhibitor of cholesterol absorption" *Elsevier Science, Atherosclerosis X,* 311–315(1995).

Wu et al., "A Novel One–Step diastereo– and Enantioselective Formation of trans–Azetidinones and Its Application to the Total Synthesis of Cholesterol Absorption Inhibitors" *J. Am. Chem. Soc.* (1999).

Ha et al., "N–Trimethylsilyl Imines: Applications to the Synthesis of β–Lactams" *J. Am. Chem. Soc.* 106(17):4819–4825 (1984).

Wentrup et al., "A stereocontrolled synthesis of (+)–Thienamycin" *J. Am. Chem. Soc.* 102:6161–6163 (1980).

Bringmann et al., "The directed cleavage of . . . β–lactams" *Synthesis* 829–831 (Oct. 1991).

Colvin et al., "Reaction of silyl . . . azetidin–2–ones" *J. Chem. Soc., Chem. Commun.* 539–540 (1985).

*Aldrich Chemical Catalog,* p. 191 (1994).

Corriu et al., "Activation of silicon–hydrogen, silicon–oxygen, silicon–nitrogen bonds in heterogeneous phase" *Tetrahedron,* 39(6):999–1009 (1983).

Bouzard et al., "Utilisation du fluorure . . . Pyridone–4–Carboxylique–3" *Tetrahedron Let.* 29(16):1931–1934 (1988).

*The Condensed Chemical Dictionary,* $10^{th}$ Ed. p. 48 (1980).

Wallbaum S. et al., 1992, "Asymmetric Syntheses with Chiral Oxazaborolidines", 3:12—1476–1495.

ENANTIOSELECTIVE SYNTHESIS OF AZETIDINONE INTERMEDIATE COMPOUNDS

This application claims priority from pending U.S. Provisional Application Serial No. 60/279,288 filed on Mar. 28, 2001.

BACKGROUND OF THE INVENTION

This invention relates to a process for producing intermediates for hydroxy-alkyl substituted azetidinones. Hydroxy-alkyl substituted azetidinones, for example, 1-(4-fluorophenyl)-3(R)-[3(S)-hydroxy-3-(4-fluorophenyl)propyl)]-4(S)-(4-hydroxyphenyl)-2-azetidinone, are described in U.S. Pat. No. 5,767,115. These compounds are useful as hypocholesterolemic agents in the treatment and prevention of atheroschlerosis.

Processes for preparing the corresponding azetidinone without the 3-hydroxy substituent are claimed in U.S. Pat. Nos. 5,728,827 and 5,561,227. Other processes for preparing 1-(4-fluorophenyl)-3(R)-[3(S)-hydroxy-3-(4-fluorophenyl)-propyl)]-4(S)-(4-hydroxyphenyl)-2-azetidinone are disclosed in U.S. Pat. Nos. 5,631,365, 5,739,321 and 6,207,822 B1 (the '822 patent).

As per the procedure described in the '822 patent, the intermediate compound of Formula I, is protected with a suitable hydroxy-protecting group, such as a silyl protecting group such as that derived from chlorotrimethylsilane (TMSCl) or t-butyldimethyl-silyl chloride (TBDMSCl). This silylated product is further reacted with a silyl-enol ether silylating agent such as bistrimethylsilyl acetamide (BSA). A cyclizing agent such as a quaternary alkyl-, aryl-alkyl or arylalkyl-alkylammonium fluoride salt is then added to cause an intra-molecular cyclization of the previously silylated compound of Formula I. Finally, the protecting groups are removed from the cyclizied compound using conventional methods, such as treatment with a dilute acid, in order to form the hypocholesterolemic azetidinone having the Formula

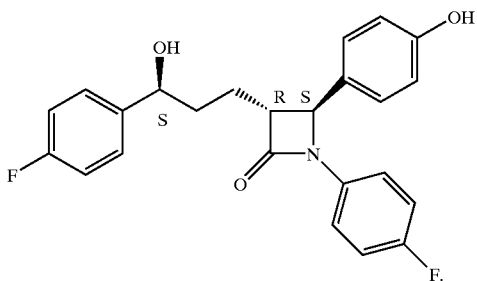

SUMMARY OF THE INVENTION

This invention provides an improved, simple, high yielding process for preparing an intermediate compound useful in the production of azetidinones. The intermediate, a compound of Formula I:

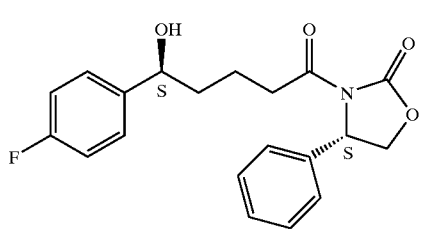

Formula I is prepared by a process which comprises:

a) mixing a compound of Formula II

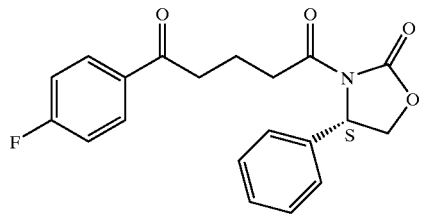

Formula II in tetrahydrofuran in the presence of an acid, or alternatively in tetrahydrofuran in the absence of an acid, to form a mixture;

b) combining the mixture of step a) with a catalyst selected from either (A) a compound selected from the group of compounds represented by Formula III, or (B) a compound of Formula IV,

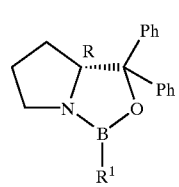

Formula III

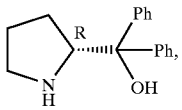

Formula IV wherein $R^1$ of Formula III is a $(C_1–C_6)$alkyl and wherein R and S indicate stereochemistry at the chiral carbons;

c) reducing the ketone adjacent to the p-fluorophenyl with a borane-tetrahydrofuran complex; and d) quenching the reaction with MeOH.

DETAILED DESCRIPTION

In one embodiment, there is described herein a process for preparing a compound of Formula I

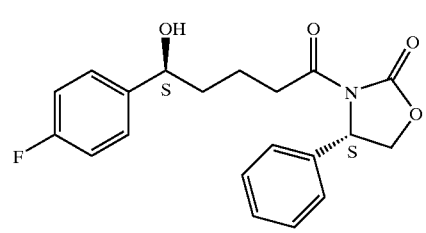

Formula I which comprises the steps (a)–(d) shown above.

In a preferred embodiment, the process comprises:

a) mixing a compound of Formula II in tetrahydrofuran in the presence of an acid to form a mixture;

b) combining the mixture of step a) with a catalyst selected from either (A) a compound selected from the group of compounds represented by Formula III, or (B) a compound of Formula IV

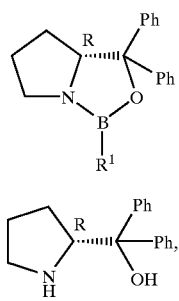

Formula III

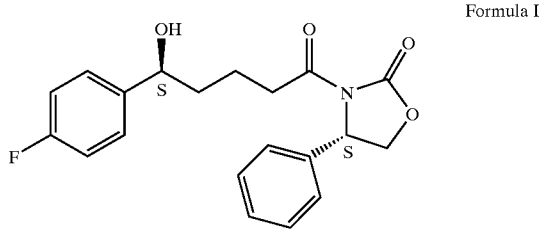

Formula IV wherein $R^1$ of Formula III is a $(C_1–C_6)$alkyl and wherein R and S indicate stereochemistry at the chiral carbons;
c) reducing the ketone adjacent to the p-fluorophenyl with a borane-tetrahydrofuran complex; and
d) quenching the reaction with MeOH.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

"Alkyl" represents a straight or branched saturated hydrocarbon chain having the designated number of carbon atoms. Where the number of carbon atoms is not specified, 1 to 6 carbons are intended.

The acid in step a) is selected from the group consisting of $BF_3.OEt_2$, $BCl_3$, p-toluene sulfonic acid, trifluoroacetic acid, methanesulfonic acid and camphorsulfonic acid.

If the catalyst of Formula IV is employed, it must be used in the presence of a trialkyl borate, preferably a trimethyl borate.

In another embodiment of the present invention, the ratio of the acid to the compound of Formula II is in a mole % of 1–10%, preferably 1–5%, more preferably in a mole % of 2–3%.

In another embodiment of the present invention, the ratio of the catalyst to the compound of Formula II of step b) is in a mole percent of 0.1–10%, preferably 1–5%, more preferably in a mole % of 2–3%.

In further embodiments of the present invention, the temperature of the reduction step c) is generally between −15 and 65° C., preferably between −10 and 55° C., more preferably between 0° and 30° C. and typically between 230 and 28° C.

In another embodiment of the invention, there is described a process for preparing a compound of Formula I Formula I

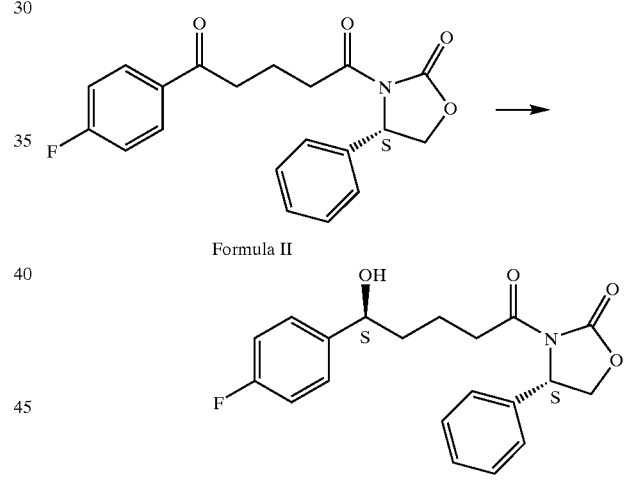

which process has no acid in step (a). The process, thus, comprises:
a) dissolving a compound of Formula II in tetrahydrofuran to form a mixture;
b) combining the mixture of step a) with a catalyst selected from either (A) a compound selected from the group of compounds represented by Formula III, or (B) a compound of Formula IV Formula III

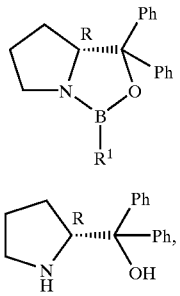

Formula IV wherein $R^1$ of Formula III is a $(C_1–C_6)$alkyl and wherein R and S indicate stereochemistry at the chiral carbons;
c) reducing the ketone adjacent to the p-fluorophenyl with a borane-tetrahydrofuran complex; and
d) quenching the reaction with MeOH.

In a preferred embodiment of the alternate process (with no acid in step (a)) described immediately above, the temperature of the reduction step c) is between 23 and 28° C.

In another embodiment of the alternate process (with no acid in step (a)) described immediately above, the ratio of the catalyst to the compound of Formula II of step b) is in a mole % of 0.1–10%, preferably 1–5%, more preferably in a mole % of 2–3%.

Formula II

Formula I

The present invention discloses a novel chemo selective and stereo selective reduction of the ketone adjacent to the p-fluorophenyl using a $BH_3$-THF complex. In a previous process patent, U.S. Pat. No. 6,207,822 B1 (the '822 patent), the disclosure of which is incorporated herein by reference thereto, there is disclosed a reduction of said ketone using $BH_3$ $Me_2S$ (BMS) complex as a reducing agent. However, use of said BMS complex may lead to environmental concerns. The replacement of BMS with borane tetrahydrofuran complex eliminates the environmental issues raised by use of the BMS complex.

However, simple replacement of $BH_3$ $Me_2S$ with $BH_3$-THF in the reduction generated a substantial amount of over-reduction of the amide bond, compared to the reduction of the ketone adjacent to the p-fluororophenyl, thus resulting in poor selectivity. Thus, initial experiments with $BH_3$-THF yielded a desirable % of desired enantiomer (SS) to the undesired enantiomer (SR), however, the solution yield was not optimized due to the production of the above-noted over-reduced by-product from the amide. Applicants found, in the present process, that reversing the addition sequence surprisingly overcame the poor chemoselectivity in the reduction. The production of the over-reduced by-product from the amide was significantly reduced while at the same time resulting in high diasteroselectivity in the product.

The new process calls for adding $BH_3$-THF to the solution of Formula II and (R)-tetrahydro-1-methyl-3,3-diphenyl-1H,3H-pyrrolo[1,2-c][1,3,2]oxazaborolidine (abbreviated as (R)-MeCBS) catalyst in THF (from Sigma-Aldrich, St. Louis, Mo.). Several experiments yielded results where the over-reduced by-product was minimized to <1% with diastereoselectivity of 97:3. In fact, the molar equivalent (eq) of $BH_3$-THF was kept to ~0.6 eq, while % molar yields were generally over 97%. Similar results could be obtained with a "in-situ" prepared catalyst using the compound of Formula IV (R-diphenylprolinol) and trimethylborate. (See reference: M. Masui, T. Shioiri, Synlett, 1997, 273).

The following examples used to prepare the compound of Formula I illustrate the present invention, although such examples should not be construed as limiting the scope of the invention. Alternative reagents and analogous processes within the scope of the invention will be apparent to those skilled in the art. The product solutions of the following examples (which contain the compound of Formula I) can be directly used as such in subsequent process steps to make hydroxy-alkyl substituted azetidinones, or in the alternative, the compounds of Formula I can be crystallized or isolated using methods known and recognized by one of ordinary skill in the art.

EXAMPLES

Abbreviations which are used in the description of the schemes, preparations and the examples are:
(R)-MeCBS=(R)-tetrahydro-1-methyl-3,3-diphenyl-1H,3H-pyrrolo[1,2-c][1,3,2]oxazaborolidine
THF=tetrahydrofuran
HPLC=High Performance Liquid Chromatography
MeOH=methanol
Atm=atmospheres
mL=milliliters
g=grams
PTSA=p-toluene sulfonic acid
CSA=(1S)-(+)-10-camphorsulfonic acid
TFA=trifluoroacetic acid
de=difference between SS % and SR %

Example 1

Acid Absent in Step(a)

Fifty (50) g of the compound of Formula II was charged into a 1000 mL three necked round bottom flask equipped with a thermometer, $N_2$ inlet and addition funnel. 500 mL THF was charged to dissolve the 50 g of the compound Formula II at about 200 to 25° C. The batch was concentrated at 1 atm to a batch volume of about 150 mL. The temperature was adjusted to about 200 to 25° C. 4.2 mL of lab pre-formed (R)-MeCBS catalyst in toluene (3 mole %) was charged. 70.4 mL of 1M borane THF complex in THF solution (from Aldrich Chemical Company, Milwaukee, Wis.) was slowly charged over 1.5 hrs at temperature between about 23° and 28° C. The batch was sampled for HPLC to monitor the progress of the reaction. After the reaction was judged complete, 20 mL of MeOH was slowly charged to keep the temperature below 25° C. in order to quench the reaction. The batch was concentrated under vacuum to afford a batch volume of about 100 mL at a temperature below 40° C. 250 mL of toluene and a solution of 5 mL sulfuric acid in 100 mL water was charged. The mixture was agitated for about 10 min. and the batch was allowed to settle. The bottom acid layer was split off. 100 mL of water was charged to wash the batch twice. The batch was concentrated under vacuum at below 50° C. to afford a volume of about 100 mL. Results varied, but in general, yields of ~99% and 95% de were obtained.

Example 2

Acid (pTSA) Present in Step (a)

Fifty (50) kg of the compound of Formula II and 0.8 kg of p-toluene sulfonic acid (PTSA) was charged into a 300 gallon glass lined reactor equipped with a thermocouple, $N_2$ inlet and feed tank. 267 kg of dry THF was charged to dissolve the 50 kg of the compound Formula II and the p-toluene sulfonic acid at about 20 to 25° C. The batch was concentrated at 1 atm to a batch volume of about 185 liters. The temperature was adjusted to about 20 to 25° C. 200 liters of THF was charged to the batch. The batch was concentrated at 1 atm to a batch volume of about 185 liters. The temperature was adjusted to about 20 to 25° C. 3.4 kg of pre-formed (R)-MeCBS catalyst in toluene (3 mole %) was charged. 70.3 kg of 1M borane THF complex in THF solution was slowly charged over 1.5 hours at a temperature range between about 23 and 28° C. The batch was sampled for HPLC to monitor the progress of the reaction. After the reaction was judged complete, using the same subsequent procedure as described in Example 1 (i.e. quenching with MeOH, vacuum concentration of the batch, etc., but in appropriate ratios of reagents for this example), the compound of Formula I was obtained in an average yield of 98.4%. A percentage yield of ~97%, a solution yield of 100% and de of 93.6% was obtained.

Example 3

Acid Present in Step (a)

Fifteen (15) kg of the compound of Formula II was charged into a 50 gallon glass lined reactor equipped with a thermocouple, $N_2$ inlet and feed tank. 150 liters of dry THF was charged to dissolve the 15 kg of the compound Formula II at about 20 to 25° C. The batch was concentrated at 1 atm to a batch volume of about 55 liters. The temperature was adjusted to about 20 to 25° C. 1.5 kg of preformed (R)-MeCBS catalyst in toluene (3 mole %) was charged. 18.55 kg of 1M borane THF complex in THF solution was charged over 1.5 hours at a temperature range between about 23 and 28° C. The batch was sampled for HPLC to monitor the progress of the reaction. After the reaction was judged complete, using the same subsequent procedure as described in Example 1 (i.e. quenching with MeOH, vacuum concentration of the batch, etc., but in appropriate ratios of reagents for this example), the compound of Formula I was obtained in a yield of 100% with a de of 95.4%.

Example 4

Acid (CSA) Present in Step (a)

Thirty (30) g of the compound of Formula II and 0.386 g (2 mole %) of (1S)-(+)-10-camphorsulfonic acid (CSA) was charged in a 500 mL 3 necked round bottom flask equipped with a thermometer, $N_2$ inlet and addition funnel. 111 mL of dry THF was charged to dissolve the 30 g of the compound Formula II, and the (1S)-(+)-10-camphorsulfonic acid at about 20 to 25° C. 2.2 mL of pre formed (R)-MCBS catalyst in toluene (3 mole %) was charged. 39.9 mL of 1M borane THF complex in THF solution was slowly charged over 1.5 hours at a temperature range between about 23 and 28° C. The batch was sampled for HPLC to monitor the progress of the reaction. After the reaction was judged complete, using the same subsequent procedure as described in Example 1 (i.e. quenching with MeOH, vacuum concentration of the batch, etc., but in appropriate ratios of reagents for this example), the compound of Formula I was obtained. Results varied, but in general, ~99% yield and ~94% de were obtained.

Example 5

Using the method described above in example 4, other acids were substituted for CSA. This group of other acids included $BF_3 \cdot OEt_2$, $BCl_3$, trifluoroacetic acid (TFA) or methansulfonic acid. Results varied, but in general, all yielded results with favorable SS:RS ratios of ~95–97% to ~3–5% and a % de range from ~91 to ~93.8%.

In general, chemical yields close to 97% and over were obtained.

We claim:
1. A process for preparing a compound of Formula I

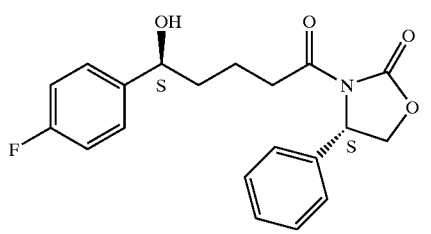

Formula I is prepared by a process which comprises:

a) mixing a compound of Formula II

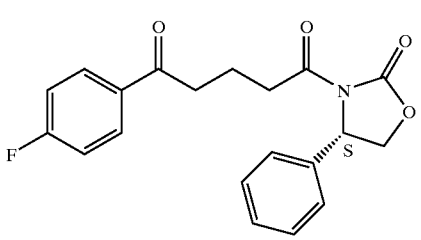

Formula II in tetrahydrofuran in the presence of an acid, or alternatively in tetrahydrofuran in the absence of an acid, to form a mixture;

b) combining the mixture of step a) with a catalyst selected from either (A) a compound selected from the group of compounds represented by Formula III, or (B) a compound of Formula IV,

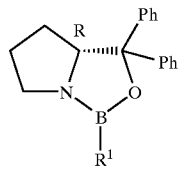

Formula III

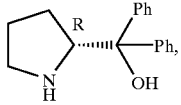

Formula IV wherein $R^1$ of Formula III is a $(C_1-C_6)$alkyl and wherein R and S indicate stereochemistry at the chiral carbons;

c) reducing the ketone adjacent to the p-fluorophenyl with a borane-tetrahydrofuran complex; and d) quenching the reaction with MeOH.

2. The process of claim 1 wherein the acid in step a) is $BF_3 \cdot OEt_2$, $BCl_3$, p-toluene sulfonic acid, trifluoroacetic acid, methanesulfonic acid, or camphorsulfonic acid.

3. The process of claim 2 wherein the catalyst of Formula IV is employed in the presence of a trialkyl borate.

4. The process of claim 3 wherein said trialkyl borate is a trimethyl borate.

5. The process of claim 2 wherein said acid is present in a 1–10 mole percent ratio with respect to said compound of Formula II.

6. The process of claim 2 wherein said acid is present in a 1–5 mole percent ratio with respect to said compound of Formula II.

7. The process of claim 2 wherein said acid is present in a 2–3 mole percent ratio with respect to said compound of Formula II.

8. The process of claim 1 wherein said catalyst is present in a 0.1–10 mole percent ratio with respect to said compound of Formula II.

9. The process of claim 1 wherein said catalyst is present in a 1–5 mole percent ratio with respect to said compound of Formula II.

10. The process of claim 1 wherein said catalyst is present in a 2–3 mole percent ratio with respect to said compound of Formula II.

11. The process of claim 1 wherein the temperature in the reduction step c) is between −15 and 65° C.

12. The process of claim 1 wherein the temperature in the reduction step c) is between −10 and 55° C.

13. The process of claim 1 wherein the temperature in the reduction step c) is between 0 and 30° C.

14. The process of claim 1 wherein the temperature in the reduction step c) is between 23 and 28° C.

15. The process of claim 1, wherein acid is present in step (a).

16. The process of claim 1, wherein acid is absent in step (a).

17. The process of claim 16 wherein the temperature in the reduction step c) is between 23 and 28° C.

18. The process of claim 16 wherein said catalyst is present in a 0.1–10 mole percent ratio with respect to said compound of Formula II.

19. The process of claim 16 wherein said catalyst is present in a 1–5 mole percent ratio with respect to said compound of Formula II.

20. The process of claim 16 wherein said catalyst is present in a 2–3 mole percent ratio with respect to said compound of Formula II.

* * * * *